US008999296B2

(12) United States Patent
Inoue et al.

(10) Patent No.: US 8,999,296 B2
(45) Date of Patent: Apr. 7, 2015

(54) METHOD OF DETECTING BLADDER CANCER

(75) Inventors: Keiji Inoue, Nankoku (JP); Masahiro Ishizuka, Saitama (JP); Tohru Tanaka, Kita-adachi-gun (JP)

(73) Assignees: Kochi University, Kochi (JP); SBI Pharmaceuticals Co., Ltd., Tokyo (JP)

( * ) Notice: Subject to any disclaimer, the term of this patent is extended or adjusted under 35 U.S.C. 154(b) by 252 days.

(21) Appl. No.: 12/988,621

(22) PCT Filed: Apr. 21, 2009

(86) PCT No.: PCT/JP2009/001821
§ 371 (c)(1),
(2), (4) Date: Oct. 19, 2010

(87) PCT Pub. No.: WO2009/130893
PCT Pub. Date: Oct. 29, 2009

(65) Prior Publication Data
US 2011/0033386 A1  Feb. 10, 2011

(30) Foreign Application Priority Data
Apr. 22, 2008  (JP) .................. 2008-111745

(51) Int. Cl.
*A61K 49/00* (2006.01)
*A61K 31/198* (2006.01)
*A61K 41/00* (2006.01)

(52) U.S. Cl.
CPC ......... *A61K 49/0021* (2013.01); *A61K 41/0061* (2013.01); *Y10S 514/814* (2013.01)

(58) Field of Classification Search
USPC .............. 424/9.6, 7.1, 59, 463; 514/410, 538, 514/561, 814, 843, 899
See application file for complete search history.

(56) References Cited

U.S. PATENT DOCUMENTS

| | | | |
|---|---|---|---|
| 5,079,262 A | 1/1992 | Kennedy et al. | |
| 5,234,940 A * | 8/1993 | Kennedy et al. | 514/410 |
| 7,135,162 B2 * | 11/2006 | Tanaka et al. | 424/9.6 |
| 7,348,361 B2 * | 3/2008 | Marti et al. | 514/561 |
| 2003/0158258 A1 | 8/2003 | Marti et al. | |
| 2004/0157905 A1 * | 8/2004 | Kennedy et al. | 514/410 |
| 2005/0031541 A1 * | 2/2005 | Gierskcky et al. | 424/9.6 |
| 2007/0249721 A1 | 10/2007 | Ito | |
| 2009/0130227 A1 | 5/2009 | Ito | |

FOREIGN PATENT DOCUMENTS

| | | |
|---|---|---|
| JP | 2731032 | 12/1997 |
| JP | 2002-512205 | 4/2002 |
| JP | 2006-124372 | 5/2006 |
| JP | 3810018 | 6/2006 |
| JP | 3991063 | 7/2007 |
| WO | WO-91/01727 | 2/1991 |
| WO | WO-99/53962 | 10/1999 |

OTHER PUBLICATIONS

Raphaela Waidelich et al., Clinical Eperience with 5-aminolevulinic acid and photodynamic therapy for refractory superficial bladder cancer, The Journal of Urology, vol. 165 (6), 1904-1907, 2001.*
James T. Dalton et al., Clinical Pharmacokenitics of 5-Aminolevulinic acid in Healthy Voluneteers and Patients at AHigh Risk for Recurrent Bladder Cancer, Journal of Pharmacology and Experimental Therapeutics, 301, 507-512, 2002.*
R. Sroka et al., Pharmacokinetics of 5-aminolevulinic acid-induced porphyrins in tumour-bearing mice, Journal of Photochemistry and Photobiology B: Biology, 34 13-19, 1996.*
Stummer Walter et al., Intraoperative Detection of Malignant Gliomas by 5-aminolevulinic acid-induced Porphyrin Fluorescence, Neurosurgery, vol. 42(3), 518-526, 1998.*
Dirk Zaak et al., Quantification of 5-aminolevulinic acid-induced fluorescence improves the specificity of bladder cancer detection, The Journal of Urology, vol. 166, 1665-1669, 2001.*
Ziya Kirkali et al. Bladder cancer: Epidermiology, Staging and Grading, and Diagnosis, Urology 66 (Suppl 6A) 4-34, 2005.*
Akasu, et al. "Study on 10 examples for identifying parathyroid glands during surgery by fluorescence emission using 5-ALA (5-Aminolevulnic Acid)" Folia endocrinologica Japonica, 2005, vol. 81, No. 1, p. 174, P-296.
Gronlund-Pakkanen, et al. "The Fluorescence Biodistribution and Kinetics of Aminolevulinic Acid Induced Protoporphyrin IX in the Bladder of a Rat Model with Orthotopic Urotehlial Carcinoma" The Journal of Urology, Apr. 2002, vol. 167, pp. 1848-1853.

(Continued)

*Primary Examiner* — Michael G Hartley
*Assistant Examiner* — Jagadishwar Samala
(74) *Attorney, Agent, or Firm* — Foley & Lardner LLP

(57) ABSTRACT

Provided is a sensitizing detection agent of an oral or intravenous administration type which enables the detection of bladder cancer with a higher sensitivity without causing pain to the patient. A sensitizing detection agent for bladder cancer comprising 5-aminolevulinic acid (ALA), a derivative thereof, or a salt of these is orally or intravenously administered, and a video camera system is inserted via the urethra and a blue light at 380-440 nm is irradiated to observe the red fluorescent part. Further, VLD-M1 is inserted and a blue light at 405 nm is irradiated to observe fluorescence intensity (relative intensity) of the red light part. For oral administration, 20 mg/kg (maximum of 1 g) of ALA is dissolved in 50 mL of a 5% glucose solution prior to the administration.

16 Claims, 2 Drawing Sheets

(56) References Cited

OTHER PUBLICATIONS

Hornung, et al. "In Vivo Detection of Metastatic Ovarian Cancer by Means of 5-Aminolevulinic Acid-Induced Fluorescence in a Rat Model" The Journal of the American Association of Gynecologic Laparoscopists, May 1998, vol. 5, No. 2, pp. 141-148.

Inoue, et al. "Clinical Experience with Intravesical Instillations of 5-Aminolevulinic Acid (5-ALA) for the Photodynamic Diagnosis Using Fluorescence Cystoscopy for Bladder Cancer" The Japanese Journal of Urology, 2006, vol. 97, No. 5, pp. 719-729.

International Search Report in PCT/JP2009/001821 dated Jun. 16, 2009.

Johansson, et al. "Laser-Induced Fluorescence Studies of Normal and Malignant Tumour Tissue of Rat Following Intravenous Injection of Delta-amino Levulinic Acid" Lasers in Surgery and Medicine, 1997, vol. 20, pp. 272-279.

Kamasaki, et al. "Photydynamic Diagnosis of Squamous Cell Carcinoma in Mouse Tongue Using 5-aminolevulinic Acid" The Journal of Japan Society for Laser Surgery and Medicine, 2001, vol. 22, No. 4, pp. 255-262.

Kennedy, et al. "Photodynamic Therapy with Endogenous Protoporphyrin IX: Basic Principles and Present Clinical Experience" Journal of Photochemistry and Photobiology, B: Biology, 1990, vol. 6, pp. 143-148.

Minami, et al. "Fluorescence diagnosis of lung cancer in a hilar area with aminolaevulnic acid" Japanese Journal of Lung Cancer, 2002, vol. 42, No. 5, p. 374, D-7.

Miyoshi, et al. "5-Aminolevulinic acid (5-ALA) o Toyo shita Shuyonai Taishabutsu Protoporphyrin-IX (Pp-IX) no Keiko Bunseki" The Journal of Japan Society for Laser Surgery and Medicine, 2002, vol. 23, pp. 81-85,87,88.

Van Staveren, et al. "Comparison of Normal Piglet Bladder Damage after PDT with Oral or Intravesical Administration of ALA", Lasers Med Sci, 2002, vol. 17, pp. 238-245.

Iinuma et al., "Biodistribution and phototoxicity of 5-aminolevulinic acid-induced PpIX in an orthotopic rat bladder tumor model," The Journal of Urology, Mar. 1, 1995, 153:802-806.

Xiao et al., "Biodistribution of Photofrin II® and 5-Aminolevulinic Acid-Induced Protoporphyrin IX in Normal Rat Bladder and Bladder Tumor Models: Implications for Photodynamic Therapy," Photochemistry and Photobiology, May 1, 1998, 67(5):573-583.

Zaak et al., "Photodynamic Diagnosis of Prostate Cancer Using 5-Aminolevulinic Acid-First Clinical Experiences," Urology, Apr. 11, 2008, 72(2):345-348.

* cited by examiner (a) pTis (bladder instillation)   (b) pTis (oral administration)

(a) pTa (bladder instillation)

(b) pTa (oral administration)

(a) pT1 (bladder instillation)

(b) pT1 (oral administration)

(a) pT3 (bladder instillation)

(b) pT2 (oral administration)

METHOD OF DETECTING BLADDER CANCER

TECHNICAL FIELD

The present invention relates to sensitizers for use in the detection of bladder cancer and to a method of detecting bladder cancer. More specifically, the present invention relates to sensitizing detection agents for diagnosing bladder cancer that comprise 5-aminolevulinic acid (ALA), a derivative thereof, or a salt of these (hereinafter may be referred to as "ALAs") that are administered orally, by bladder instillation, by intravenous injection or the like, and to a method of detecting bladder cancer with the use of the sensitizing detection agents, etc.

BACKGROUND ART

Since Professor Kennedy of Queens University, Canada, reported in 1986 that skin cancer can be treated by application of ALA and light irradiation (e.g., see Nonpatent Document 1), there have been reports on methods for diagnosis and treatment using ALA for lesions at various sites, etc. For example, a tumor diagnosing agent developed out of the finding that in vivo administration of ALA, a derivative thereof, or a salt of these (ALAs) causes accumulation of protoporphyrin IX (PpIX), which is induced by ALAs, in the cancer and thus a fluorescence emission is caused in response to light irradiation (e.g., see Patent Document 1), and a tumor diagnosing agent wherein ALAs are administered in vivo to detect PpIX that emits fluorescence in the serum or urine in response to light irradiation (e.g., see Patent Document 2) are proposed. It is known regarding a brain tumor that the tumor site can be identified by orally administering ALAs and subjecting the affected area to light irradiation after the craniotomy. This is based on that because the blood-brain barrier at the site leading to the tumor has been destroyed by the tumor, PpIX is considered to accumulate in a tumor selective manner even by the oral administration. With regard to other cancers, it has been reported that diagnosis can be made by a direct application of ALAs for skin cancer and by holding a solution of ALAs in the mouth for oral cancer.

Further, as for bladder, it is known that bladder cancer can be detected by filling a sensitizer solution containing ALAs into the bladder via the urethra, and then by conducting light irradiation after a certain period of time to observe fluorescence with a cystoscope (e.g., see Nonpatent Document 2). Moreover, formulated drugs that can be used for diagnosis or treatment using such as ALA esters among the ALAs are proposed for the purpose of, for example, shortening the retention time after bladder instillation (e.g., see Patent Document 3). These detection methods exhibit a higher detection sensitivity to cancers compared to other detection methods for bladder cancer, for example, as compared to the endoscopic diagnosis under white light. Therefore, these detection methods can be said as being effective in improving the enucleation rate in endoscopic surgeries.

In addition, there is proposed a hair restorer which contains as the active components one or more compounds selected from 5-aminolevulinic acid, a salt thereof and an ester derivative of these, along with an iron compound (e.g., see Patent Document 4) and a preventive/ameliorating drug for skin roughness (e.g., see Patent Document 5).

Patent Document 1: Japanese Patent No. 2731032
Patent Document 2: Japanese Laid-Open Patent Application No. 2006-124372
Patent Document 3: Published Japanese translation of PCT international publication No. 2002-512205
Patent Document 4: Japanese Patent No. 3810018
Patent Document 5: Japanese Patent No. 3991063
Nonpatent Document 1: J. C Kennedy, R. H Pottier and D C pross, Photodynamic therapy with endogeneous protoprophyrin IX: basic principles and present clinical experience, J. Photochem., Photobiol. B: Biol., 6 (1990) 143-148
Nonpatent Document 2: Hirofumi Inoue, Hisashi Karashima, Masayuki Kamata, Taro Shuin, Mutsumi Kurabayashi, Yuji Otsuki, Photodynamic diagnosis of bladder cancer using fluorescent cystoscope by bladder instillation of 5-aminolevulinic acid (5-ALA), Journal of The Japanese Urological Association, Vol. 97, pp. 719-729

DISCLOSURE OF THE INVENTION

Object to be Solved by the Invention

Detection methods using ALA or derivatives thereof that are currently in practical use have not yet reached the level of capably detecting early cancers. Moreover, it incurs burden on the patients to fill the bladder with a solution via the urethra and to retain the situation for a certain period of time. Particularly because the retention for a certain period of time causes unbearable pain to the patients such that they are forced to endure sometime even for as long as several hours while having urge to urinate, the improvement in these methods have been longed for.

Means to Solve the Object

The present inventors have made a keen study on methods of detecting bladder cancer that employ oral administration, when oral administration has been believed as inapplicable to detection of cancers except in those sites to which oral administration has been explained as being applicable due to the blood-brain barrier selectivity. As a result of the study, it was so surprisingly discovered that the detection of bladder cancer is possible by employing oral or intravenous administration of ALAs even where the blood-brain barrier selectivity cannot be expected to be involved in bladder cancer. Moreover, by widely examining such as what to be selected from among ALAs, the doses, a time period from administration of ALAs to the detection, the present inventors have successfully achieved a much higher detection sensitivity as compared to a conventionally performed injection of solution of ALAs via the urethra. The present invention has thus completed.

Specifically, the present invention relates to: (1) a sensitizer which is an orally administered agent for detecting bladder cancer and which comprises 5-aminolevulinic acid (ALA), a derivative thereof, or a salt of these, (2) a sensitizer which is an intravenously injected agent for detecting bladder cancer and which comprises 5-aminolevulinic acid (ALA), a derivative thereof, or a salt of these, and (3) the sensitizer according to (1) or (2), wherein the bladder cancer is at a disease stage of pTis (intraepithelial cancer), pTa (without invasion), pT1 (with invasion to submucosal connective tissue), pT2 (with muscle invasion), or pT3 (with invasion to pericystic adipose tissue).

The present invention further relates to (4) a method of detecting bladder cancer, wherein the sensitizer according to any one of (1) to (3) is used, (5) a method of using 5-aminolevulinic acid (ALA), a derivative thereof, or a salt of these for producing a sensitizer which is an orally administered agent for detecting bladder cancer, and (6) a method of using 5-aminolevulinic acid (ALA), a derivative thereof, or a salt of these for producing a sensitizer which is an intravenously injected agent for detecting bladder cancer.

BEST MODE OF CARRYING OUT THE INVENTION

Figure 1:
FIG. 1 is an image after the bladder instillation of ALA.

A sensitizer as an orally administered agent and a sensitizer as an intravenously injected agent for the detection of bladder cancer of the present invention are not particularly limited as long as the agents comprise at least a single kind of ALAs. Also, a method of detecting bladder cancer of the present invention is not particularly limited as long as it is a method using a sensitizer which is an orally administered or intravenously injected agent comprising one or more kinds of ALAs. The ALAs can be produced by any known method such as production by chemical synthesis, production by microorganisms, and production using enzymes. The present invention further relates to a method of using ALAs for production of a sensitizer, which is an orally administered or intravenously injected agent, for the detection of bladder cancer.

Among ALAs, an ALA derivative is exemplified by those ALAs having an ester group and an acyl group, where the preferred examples include the combinations of methyl ester group and formyl group, methyl ester group and acetyl group, methyl ester group and n-propanoyl group, methyl ester group and n-butanoyl group, ethyl ester group and formyl group, ethyl ester group and acetyl group, ethyl ester group and n-propanoyl group, and ethyl ester group and n-butanoyl group.

Among ALAs, examples of a salt of ALA or its derivative include: an acid addition salt such as hydrochloride, hydrobromate, hydroiodide, phosphate, nitrate, hydrosulfate, acetate, propionate, toluenesulfonate, succinate, oxalate, lactate, tartrate, glycolate, methanesulfonate, butyrate, valerate, citrate, fumarate, maleate and malate; a metallic salt such as sodium salt, potassium salt and calcium salt; ammonium salt; and alkylammonium salt. Preferably exemplified among these is ALA hydrochloride. When for use, these salts are used in the form of a solution and act in a similar manner to ALA and its derivatives. ALAs mentioned above may form a hydrate or a solvate and may be used either alone or in appropriate combination of two or more kinds.

There are orally administered type and intravenously injected type for a sensitizer (a sensitizing detection agent) of the present invention. Form of a sensitizer of an orally administered type of the present invention is exemplified by powders, granules, tablet, capsule, syrup and suspension. Form of a sensitizer of an intravenously injected type of the present invention is exemplified by an injection solution and an infusion agent. Other components such as a medicinal component, nutrient, carrier, etc. may be added to a sensitizer of the present invention according to need. For example, various compounding ingredients for preparation of a drug may be added such as a pharmacologically acceptable common carrier, binder, stabilizer, solvent, dispersant, expander, excipient, diluent, pH buffer, disintegrant, solubilizer, solubilizing adjuvant, isotonic agent, etc.

When preparing a sensitizer of the present invention as an aqueous solution, care should be paid not to result in an alkaline solution which leads to the degradation of ALAs. When the solution turns to alkaline, degradation of the active ingredients can be avoided by removing oxygen. Organic or inorganic, solid or liquid carrier materials that are suitable for intake, pharmacologically acceptable, and inactive under normal conditions may be used as a carrier to be compounded in a sensitizer of the present invention. Specific examples of the carrier include crystalline cellulose, gelatin, lactose, starch, magnesium stearate, talc, vegetable and animal fat, oil, gum, and polyalkylene glycol. The most desired among ALAs to be contained in a sensitizer of the present invention are 5-aminolevulinic acid, 5-aminolevulinic acid methyl ester, 5-aminolevulinic acid ethyl ester, 5-aminolevulinic acid propyl ester, 5-aminolevulinic acid butyl ester and 5-aminolevulinic acid pentyl ester, or their hydrochloride, phosphate, hydrosulfate, etc.

Preferred ways of administering a sensitizer of the present invention are oral administration including sublingual administration and intravenous injection including infusion. Amount of ALAs contained in the sensitizer is, as a total ALAs in terms of moles, 0.1-100 mg, preferably 1-100 mg and more preferably 10-50 mg per 1 kg body weight in ALA hydrochloride equivalent.

In the detection method of the present invention, retention time from administration of a sensitizer to the detection is 30 min to 8 hours, preferably 1-6 hours and more preferably 2-5 hours. A detection required for the present invention may be any detection that employs light irradiation and detecting fluorescence. For example, detection can be done by detecting fluorescence at approximately 600-700 nm after irradiating an excitation light approximately at 380-430 nm which is a so-called soret band light. Not only a mechanical detection but a macroscopic detection and CCD camera detection are also useful.

The present invention is explained in more detail in the following Examples, while the technical scope of the present invention shall not be restricted to these exemplifications.

Example 1

Intraoperative diagnosis using 5-aminolevulinic acid hydrochloride (ALA-HCl) was carried out for two subjects who are in the almost same progression stage of bladder cancer. The subjects were administered ALA-HCl respectively by bladder instillation and by oral intake. Bladder instillation was conducted on the day of operation by dissolving 1.5 g of ALA-HCl in 50 mL of a 8.4% sodium bicarbonate (sodium hydrogen carbonate: $NaHCO_3$) to adjust pH (median pH of 8.0 (pH 7.8-8.2)), filtrating the dissolved ALA-HCl solution with a 0.22 μm filter, and then injecting this dissolved solution (50 mL) into the bladder of a subject. Retention time in the bladder was set for 120-150 min (average of about 90 min) and ALA was eliminated just prior to the operation. On the other hand, oral intake was carried out by dissolving ALA (maximum of 1 g) in 50 mL of a 5% dextrose solution to 20 mg/kg, and the ALA dissolved solution (50 mL) was orally administered to the other subject in the morning (4 hours before commencement of the operation) without giving breakfast. Diagnosis was conducted based on the diagnostic imaging and fluorescent intensity with the use of a video camera system: Endovision TELECAM SL/IPM-PPDSystem (KARL STORZ) and VLD-M1 (M&M). The video camera system was inserted via the urethra and the red light part was observed after irradiating a blue fluorescence at 380-440 nm. Further, VLD-M1 was inserted and fluorescence intensity (relative intensity) at the red light part was observed after irradiating a blue fluorescence at 405 nm.

Figure 2:
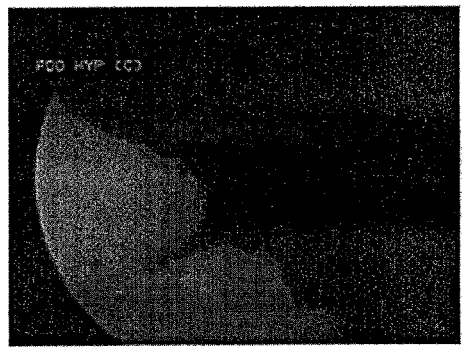
FIG. 2 is an image after the oral intake (oral administration) of ALA.
Figure 3:
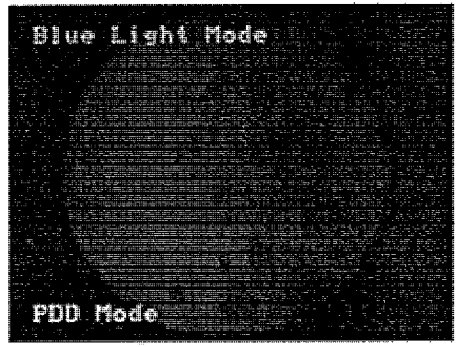
FIG. 3 shows the images of when ALA was injected into the bladder (a) and when orally administered (b) to pTis (intraepithelial cancer) patients.
Figure 3:
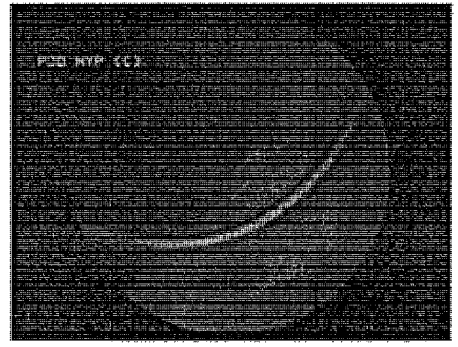
Figure 4:
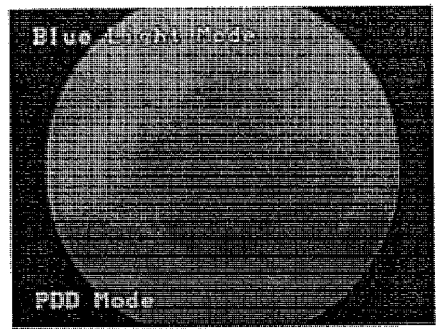
FIG. 4 shows the images of when ALA was injected into the bladder (a) and when orally administered (b) to pTa (without invasion) patients.
Figure 4:
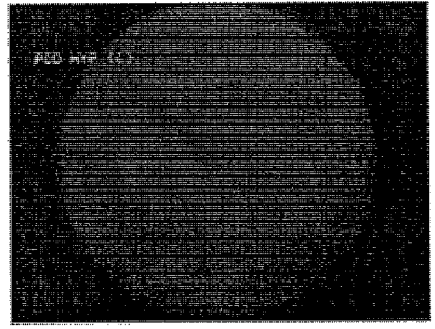
Figure 5:
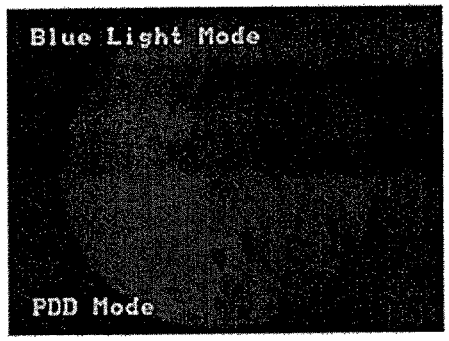
FIG. 5 shows the images of when ALA was injected into the bladder (a) and when orally administered (b) to pT1 (with invasion to submucosal connective tissue) patients.
Figure 5:
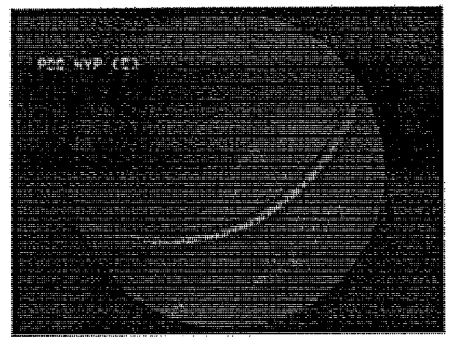
Figure 6:
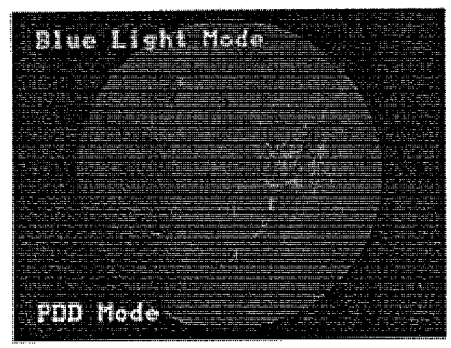
FIG. 6 shows the images of when ALA was injected into the bladder of a pT3 (with invasion to pericystic adipose tissue) patient (a) and when orally administered to a pT2 (with muscle invasion) patient (b).
Figure 6:
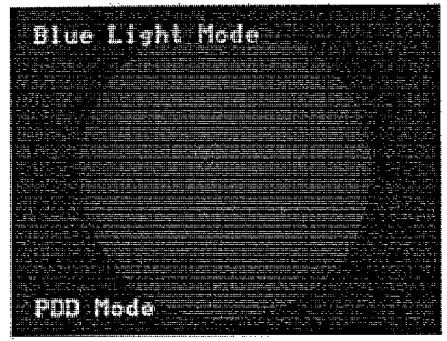

As a result, it was confirmed as shown in FIGS. 1 and 2 that the site of bladder cancer can be more remarkably identified in the case of oral intake than in the case of bladder instillation. In addition, at 635 nm which is the excitation wavelength for protoporphyrin IX (PpIX), it was confirmed as shown in Table 1 that the fluorescence intensity was higher in the case of oral intake than in the case of bladder instillation. This result confirmed that ALA is taken in bladder cancer by the oral intake and is metabolized so that the amount converted to protoporphyrin IX can be easily determined and bladder cancer can be easily identified.

TABLE 1

Comparison of fluorescence intensity (relative intensity) by VLD-M1

|  | Bladder instillation of ALA | Oral intake of ALA |
|---|---|---|
| Relative intensity | 20153 | 48623 |

As is obvious from the above, not only the present invention reduces pain of the patients as compared to conventional methods, it also apparently exhibits a higher sensitivity and is practically useful.

Example 2

ALA was injected into the bladder or administered orally similarly to Example 1 to bladder cancer patients who had been grouped according to the disease stages based on the intramural invasion depth of the primary tumor: 6 cases of pTis (intraepithelial cancer), 27 cases of pTa (without invasion), 9 cases of pT1 (with invasion to submucosal connective tissue), 6 cases of pT2 (with muscle invasion), 2 cases of pT3 (with invasion to pericystic adipose tissue) (50 cases for total number of patients). In all the cases, fluorescence was more intensive when ALA was orally administered than when injected into the bladder (see FIGS. 3, 4, 5 and 6). This confirmed that oral administration is effective in a diagnosis method for bladder cancer at every disease stage.

INDUSTRIAL APPLICABILITY

It is possible to detect bladder cancer with a higher sensitivity without causing pain to the patients by using a sensitizer of the present invention that can be orally or intravenously administered. A highly toxic ALA hexyl ester hydrochloride has been conventionally used in order to shorten retention time of the drug solution in the bladder as much as possible to reduce pain of the patient, but it has become possible to use other less toxic ALAs instead.

The invention claimed is:

1. A method of detecting bladder cancer comprising the sequential steps of:
   (a) orally administering to a mammal a bladder cancer detecting sensitizer which comprises 5-aminolevulinic acid (ALA), a derivative thereof, or a salt of these, wherein the oral administration of the sensitizer to the mammal delivers 10 to 50 mg ALA per kilo body weight in ALA hydrochloride equivalent or a molar equivalent of the derivative or the salt thereof;
   (b) irradiating the mammalian bladder with an excitation light of 380-440 nm; and
   (c) detecting fluorescence intensity at red light part of the bladder,
   wherein steps (b) and (c) are performed between 2 hours and less than 5 hours after step (a).

2. The detection method according to claim 1, wherein the 5-aminolevulinic acid (ALA), a derivative thereof, or a salt of these is 5-aminolevulinic acid or a salt thereof.

3. The detection method according to claim 1, wherein the bladder cancer is at a disease stage of pTis (intraepithelial cancer), pTa (without invasion), pT1 (with invasion to submucosal connective tissue), pT2 (with muscle invasion), or pT3 (with invasion to pericystic adipose tissue).

4. The detection method according to claim 3, wherein the 5-aminolevulinic acid (ALA), a derivative thereof, or a salt of these is 5-aminolevulinic acid or a salt thereof.

5. A method of detecting bladder cancer comprising the sequential steps of:
   (a) intravenously injecting to a mammal a bladder cancer detecting sensitizer which comprises 5-aminolevulinic acid (ALA), a derivative thereof, or a salt of these, wherein the intravenous injection of the sensitizer to the mammal delivers 10 to 50 mg ALA per kilo body weight in ALA hydrochloride equivalent or a molar equivalent of the derivative or the salt thereof;
   (b) irradiating the mammalian bladder with an excitation light of 380-440 nm; and
   (c) detecting fluorescence intensity at red light part of the bladder,
   wherein steps (b) and (c) are performed between 2 hours and less than 5 hours after step (a).

6. The detection method according to claim 5, wherein the 5-aminolevulinic acid (ALA), a derivative thereof, or a salt of these is 5-aminolevulinic acid or a salt thereof.

7. The detection method according to claim 5, wherein the bladder cancer is at a disease stage of pTis (intraepithelial cancer), pTa (without invasion), pT1 (with invasion to submucosal connective tissue), pT2 (with muscle invasion), or pT3 (with invasion to pericystic adipose tissue).

8. The detection method according to claim 7, wherein the 5-aminolevulinic acid (ALA), a derivative thereof, or a salt of these is 5-aminolevulinic acid or a salt thereof.

9. A method of using 5-aminolevulinic acid (ALA), a derivative thereof, or a salt of these for producing an orally administrable bladder cancer detecting sensitizer, wherein oral administration of the sensitizer to a mammal delivers 10 to 50 mg ALA per kilo body weight in ALA hydrochloride equivalent or a molar equivalent of the derivative or the salt thereof prior to detecting fluorescence intensity in the bladder, and wherein the time from the oral administration of the sensitizer to the detection is between 2 hours to less than 5 hours.

10. The method according to claim 9, wherein the 5-aminolevulinic acid (ALA), a derivative thereof, or a salt of these is 5-aminolevulinic acid or a salt thereof.

11. The detection method according to claim 9, wherein the bladder cancer is at a disease stage of pTis (intraepithelial cancer), pTa (without invasion), pT1 (with invasion to submucosal connective tissue), pT2 (with muscle invasion), or pT3 (with invasion to pericystic adipose tissue).

12. The detection method according to claim 11, wherein the 5-aminolevulinic acid (ALA), a derivative thereof, or a salt of these is 5-aminolevulinic acid or a salt thereof.

13. A method of using 5-aminolevulinic acid (ALA), a derivative thereof, or a salt of these for producing an intravenously injectable bladder cancer detecting sensitizer, wherein intravenous injection of the sensitizer to a mammal delivers 10 to 50 mg ALA per kilo body weight in ALA hydrochloride equivalent or a molar equivalent of the derivative or the salt thereof prior to detecting fluorescence intensity in the bladder, and wherein the time from the intravenous injection of the sensitizer to the detection is between 2 hours to less than 5 hours.

14. The method according to claim 13, wherein the 5-aminolevulinic acid (ALA), a derivative thereof, or a salt of these is 5-aminolevulinic acid or a salt thereof.

15. The detection method according to claim 13, wherein the bladder cancer is at a disease stage of pTis (intraepithelial cancer), pTa (without invasion), pT1 (with invasion to submucosal connective tissue), pT2 (with muscle invasion), or pT3 (with invasion to pericystic adipose tissue).

16. The detection method according to claim 15, wherein the 5-aminolevulinic acid (ALA), a derivative thereof, or a salt of these is 5-aminolevulinic acid or a salt thereof.

* * * * *